US012793832B2

(12) United States Patent
Yoon et al.

(10) Patent No.: US 12,793,832 B2
(45) Date of Patent: Nov. 10, 2026

(54) VIDEO CONFERENCE IMAGE-BASED SOCIAL ANXIETY TREATMENT SYSTEM USING BIOFEEDBACK AND EXPOSURE THERAPY, AND NON-TRANSITORY RECORDING MEDIUM HAVING, RECORDED THEREON, PROGRAM FOR EXECUTING METHOD FOR SAME

(71) Applicant: KOREA UNIVERSITY RESEARCH AND BUSINESS FOUNDATION, Seoul (KR)

(72) Inventors: Ho Kyoung Yoon, Seoul (KR); June Kang, Goyang-si (KR)

(73) Assignee: Korea University Research and Business Foundation, Seoul (KR)

( * ) Notice: Subject to any disclaimer, the term of this patent is extended or adjusted under 35 U.S.C. 154(b) by 256 days.

(21) Appl. No.: 18/270,441

(22) PCT Filed: Dec. 14, 2021

(86) PCT No.: PCT/KR2021/018962
§ 371 (c)(1),
(2) Date: Jun. 29, 2023

(87) PCT Pub. No.: WO2022/145811
PCT Pub. Date: Jul. 7, 2022

(65) Prior Publication Data
US 2024/0062876 A1 Feb. 22, 2024

(30) Foreign Application Priority Data
Dec. 30, 2020 (KR) ........................ 10-2020-0187503

(51) Int. Cl.
*G16H 20/70* (2018.01)
*A61B 5/00* (2006.01)
(Continued)

(52) U.S. Cl.
CPC ........... *G16H 20/70* (2018.01); *A61B 5/0077* (2013.01); *A61B 5/163* (2017.08); *A61B 5/165* (2013.01); *G16H 80/00* (2018.01)

(58) Field of Classification Search
CPC .... A61M 2205/505; A61M 2205/3592; A61M 2205/3584; A61M 2021/005; G16H 40/67;
(Continued)

(56) References Cited

U.S. PATENT DOCUMENTS 5,343,871 A 9/1994 Bittman et al.
10,446,055 B2 * 10/2019 Gupta .................. G10L 15/187
(Continued)

FOREIGN PATENT DOCUMENTS

CN 111596761 A 8/2020
KR 10-2001-0099277 A 11/2001
(Continued)

OTHER PUBLICATIONS

Livia Petrescu, Integrating Biosignals Measurement in Virtual Reality Environments for Anxiety Detection,PublishedDec. 10, 2020, MDPI, SENSORS, pp. 1-31 (Year: 2020).*
(Continued)

*Primary Examiner* — Mamon Obeid
*Assistant Examiner* — Teresa S Williams
(74) *Attorney, Agent, or Firm* — NSIP Law

(57) ABSTRACT

Disclosed are a video conference image-based social anxiety treatment system using biofeedback and exposure therapy, and a recording medium having, recorded thereon, a program for executing a method for same. According to an embodiment of the inventive concept, a social anxiety treatment system includes an anxiety level measurement unit that measures an anxiety level of a subject, which is a target of social anxiety treatment, while the subject performs a
(Continued)

speech task through a video conference, a video conference image provision unit that provides the subject with video conference images including a participant connected to and participating in the video conference and a virtual participant prepared in advance, and an exposure therapy level adjustment unit that adjusts an exposure therapy level according to the anxiety level of the subject, which changes according to the video conference images.

11 Claims, 9 Drawing Sheets

(51) Int. Cl.
*A61B 5/16* (2006.01)
*G16H 80/00* (2018.01)

(58) Field of Classification Search
CPC ........ G16H 30/40; G16H 80/00; G16H 20/70; G06V 40/174; G06V 10/82
USPC ........................................................ 705/3
See application file for complete search history.

(56) References Cited

U.S. PATENT DOCUMENTS 10,869,626 B2 12/2020 Krupat et al.
11,785,180 B2 * 10/2023 Peters .................... G06V 20/41 348/14.09
2016/0077547 A1 3/2016 Aimone et al.
2017/0319123 A1 11/2017 Voss et al.
2020/0302825 A1 * 9/2020 Sachs .................. H04N 21/472
2021/0022657 A1 * 1/2021 Voss ..................... A61B 5/0036

FOREIGN PATENT DOCUMENTS

KR 10-2018-0095148 A 8/2018
KR 10-2019-0020418 A 3/2019
KR 10-1953612 B1 3/2019
KR 10-2020598 B1 9/2019
KR 10-2170379 B1 10/2020
WO WO 2015/121253 A1 8/2015
WO WO-2025061903 A1 * 3/2025 ............. H04N 7/147

OTHER PUBLICATIONS

Lee et al. "Virtual reality system for treatment of the fear of public speaking using image-based rendering and moving pictures" *Cyberpsychology & behavior* vol. 5 No. 3. 2002 (pp. 191-195).
Warnock-Parkers et al. "Treating social anxiety disorder remotely with cognitive therapy" *The Cognitive Behaviour Therapist* vol. 13. Jul. 16, 2020 (pp. 1-22).
Wang, Yuntao, "Face-changing Technology and Virtual Reality Technology-Based Method and Device for Simulating Speech", Aug. 28, 2020, (7 Pages in English).
Extended European Search Report Issued on Jan. 7, 2025, in Counterpart European Patent Application No. 21915609.8 (12 Pages in English).

* cited by examiner

VIDEO CONFERENCE IMAGE-BASED SOCIAL ANXIETY TREATMENT SYSTEM USING BIOFEEDBACK AND EXPOSURE THERAPY, AND NON-TRANSITORY RECORDING MEDIUM HAVING, RECORDED THEREON, PROGRAM FOR EXECUTING METHOD FOR SAME

CROSS REFERENCE TO RELATED APPLICATIONS

This application is a U.S. National Stage Application of International Application No. PCT/KR2021/018962, filed on Dec. 14, 2021, which claims the benefit under 35 USC 119 (a) and 365(b) of Korean Patent Application No. 10-2020-0187503, filed on Dec. 30, 2020, in the Korean Intellectual Property Office, the entire disclosure of which is incorporated herein by reference for all purposes.

TECHNICAL FIELD

The inventive concept relates to a video conference image-based social anxiety treatment system using biofeedback and exposure therapy and a non-transitory recording medium having, recorded thereon, a program for executing the method.

The inventive concept is derived from research conducted as part of (science and engineering) (type 1-1) mid-level research of the Ministry of Science and ICT (Project No.; 2002321, Project No.; 2020R1A2C100807211, Research project name; Post-traumatic stress disorder treatment technology Development using machine learning-based non-invasive autonomic nervous system control technique, project management institution; National Research Foundation of Korea, task performing institution; Korea University Industry-University Cooperation Foundation, research period; 2020 Mar. 1-2021 Feb. 28). Meanwhile, there is no property interest of the Korean government in any aspect of the inventive concept.

BACKGROUND ART

In recent years, the percentage of people suffering from social anxiety disorder has been increased. The social anxiety disorder is one of anxiety disorders, and is characterized by a fear of social situations involving interaction with other people and a tendency to avoid these situations. The social anxiety disorder indicates situations in which a person is unrealistically and intensely afraid even in social situations where the person feels that strangers are watching her/him attentively, or where the person encounters other people.

Various treatment methods have been studied to overcome this social anxiety disorder. Among the various treatment methods, exposure therapy is known to be effective in relieving social anxiety symptoms. The exposure therapy refers to a treatment method that creates a simulated situation in which a person experiencing severe anxiety reveals the presentation for treatment when speaking in front of people, and exposes the person to a situation that forces the person to make presentations while the number of audiences is gradually increased, thereby reducing anxiety about the situation in which the person becomes accustomed to speaking in front of the public and becomes blunt. However, a conventional exposure therapy method is simply a method of speaking in front of an audience. Accordingly, the conventional exposure therapy method is expensive, time-consuming, and inaccessible.

DETAILED DESCRIPTION OF THE INVENTION

Technical Problem

An aspect of the inventive concept provides a video conference image-based social anxiety treatment system using biofeedback and exposure therapy and a non-transitory recording medium recording a program for executing the method.

Moreover, an aspect of the inventive concept provides a social anxiety treatment system, which adjusts a video conference image depending on an anxiety level of a social anxiety treatment subject, and a non-transitory recording medium recording a program for executing the method.

Furthermore, an aspect of the inventive concept provides a social anxiety treatment system, which is capable of increasing the realism of a video conference while including a virtual participant in the video conference image, and a non-transitory recording medium recording a program for executing the method.

Technical Solution

According to an embodiment of the inventive concept, a video conference image-based social anxiety treatment system using biofeedback and exposure therapy includes an anxiety level measurement unit that measures an anxiety level of a subject, which is a target of social anxiety treatment, while the subject performs a speech task through a video conference, a video conference image provision unit that provides the subject with video conference images including a participant connected to and participating in the video conference and a virtual participant prepared in advance, and an exposure therapy level adjustment unit that adjusts an exposure therapy level according to the anxiety level of the subject, which changes according to the video conference images.

The video conference images include a first face image of the participant and a second face image of the virtual participant. The exposure therapy level adjustment unit is configured to adjust an exposure rate of the first face image or an expression of the second face image, depending on the anxiety level of the subject.

The second face image may include a plurality of virtual participant images having different facial expressions and anxiety-inducing levels. The plurality of virtual participant images may include a plurality of videos that are previously obtained from a plurality of virtual participants having an anxious facial expression, an indifferent facial expression, and a bright facial expression. The exposure therapy level adjustment unit may be configured to adjust exposure ratios of the plurality of virtual participant images depending on the anxiety level of the subject.

The first face image may include a plurality of real-time participant images of a plurality of participants actually participating in the video conference by using a participant terminal. The exposure therapy level adjustment unit may be configured to provide the participant terminal with a guide phrase for changing an expression of the participant depending on the anxiety level of the subject.

The exposure therapy level adjustment unit may include an anxiety-inducing level measurement unit that measures an anxiety-inducing level of the facial expression of the participant from the plurality of real-time participant images exposed to the subject through the video conference, a first image selection unit that selects at least one first image from among the plurality of real-time participant images and a plurality of first virtual participant images based on an anxiety-inducing level from measuring each of the plurality of real-time participant images and an anxiety-inducing level of each of the plurality of first virtual participant images being exposed to the subject through the video conference, a second image selection unit that selects at least one second image from among a plurality of second virtual participant images, which are not exposed to the subject through the video conference, based on the anxiety level of the subject, and an image switching unit that switches the first image, which is being exposed to the subject through the video conference, to the second image and exposes the second image to the subject through the video conference.

The video conference image provision unit may be configured to randomly and sequentially provide the plurality of real-time participant images and the plurality of first virtual participant images so as to simulate real-time access to the video conference at a participation time of the subject.

The image switching unit may be configured to randomly and sequentially switch a plurality of first images to a plurality of second images so as to simulate the real-time access to the video conference when the plurality of first image is switched into the plurality of second image.

The exposure therapy level adjustment unit may include a first anxiety-inducing level calculation unit that calculates a first anxiety-inducing level by summing anxiety-inducing levels from respectively measuring the plurality of real-time participant images, a second anxiety-inducing level calculation unit that calculates a second anxiety-inducing level by summing anxiety-inducing levels from respectively measuring the plurality of first virtual participant images, and a virtual participant image selection unit that selects the plurality of first virtual participant images from among the plurality of virtual participant images such that a change amount of the second anxiety-inducing level offsets a change amount of the first anxiety-inducing level.

In an embodiment of the inventive concept, the video conference image-based social anxiety treatment system may further include a bio-signal collection unit configured to collect a bio-signal of the subject. The bio-signal collection unit may include a wearable terminal worn on the subject and collecting the bio-signal of the subject. The anxiety level measurement unit may measure the anxiety level of the subject from the bio-signal of the subject collected by the wearable terminal while the subject performs the speech task.

In another embodiment of the inventive concept, the anxiety level measurement unit may obtain a user image by photographing the subject by a camera while the subject performs the speech task, and may measure the anxiety level of the subject by analyzing a facial expression of the subject and an action of the subject in the user image.

According to an embodiment of the inventive concept, in a video conference image-based social anxiety treatment system, when the subject selects one category from among various categories of topics of the speech task, a sub-topic of the selected category is randomly selected and then is presented in a form of a pop-up.

According to an embodiment of the inventive concept, a non-transitory recording medium having, recorded thereon, a program for executing a video conference image-based social anxiety treatment method using biofeedback and exposure therapy is provided. The social anxiety treatment method includes measuring an anxiety level of a subject, which is a target of social anxiety treatment, while the subject performs a speech task through a video conference, providing the subject with video conference images of a participant or a virtual participant, which participates in the video conference, and adjusting an exposure therapy level according to the anxiety level of the subject, which changes according to the video conference images.

The adjusting of the exposure therapy level may include adjusting an exposure rate of the first face image or an expression of the second face image, depending on the anxiety level of the subject, adjusting exposure ratios of the plurality of virtual participant images depending on the anxiety level of the subject, or providing the participant terminal with a guide phrase for changing an expression of the participant depending on the anxiety level of the subject.

The adjusting of the exposure therapy level may include measuring an anxiety-inducing level of the facial expression of the participant from the plurality of real-time participant images exposed to the subject through the video conference, selecting at least one first image from among the plurality of real-time participant images and a plurality of first virtual participant images based on an anxiety-inducing level from measuring each of the plurality of real-time participant images and an anxiety-inducing level of each of the plurality of first virtual participant images being exposed to the subject through the video conference, selecting at least one second image from among a plurality of second virtual participant images, which are not exposed to the subject through the video conference, based on the anxiety level of the subject, and switching the first image, which is being exposed to the subject through the video conference, to the second image and exposing the second image to the subject through the video conference.

The providing of the subject with the video conference images may include randomly and sequentially providing the plurality of real-time participant images and the plurality of first virtual participant images so as to simulate real-time access to the video conference at a participation time of the subject, and randomly and sequentially switching a plurality of first images to a plurality of second images so as to simulate the real-time access to the video conference when the plurality of first image is switched into the plurality of second image.

The adjusting of the exposure therapy level may include calculating a first anxiety-inducing level by summing anxiety-inducing levels from respectively measuring the plurality of real-time participant images and calculating a change amount of the first anxiety-inducing level, calculating a second anxiety-inducing level by summing anxiety-inducing levels from respectively measuring the plurality of first virtual participant images and calculating a change amount of the second anxiety-inducing level, and selecting the plurality of first virtual participant images from among the plurality of virtual participant images such that the change amount of the second anxiety-inducing level offsets the change amount of the first anxiety-inducing level.

Advantageous Effects of the Invention

According to an embodiment of the inventive concept, it is possible to provide a video conference image-based social anxiety treatment system using biofeedback and exposure therapy and a non-transitory recording medium recording a program for executing the method.

Moreover, according to an embodiment of the inventive concept, it is possible to provide a social anxiety treatment system, which adjusts a video conference image depending on an anxiety level of a social anxiety treatment subject, and a non-transitory recording medium recording a program for executing the method.

Furthermore, according to an embodiment of the inventive concept, it is possible to provide a social anxiety treatment system, which is capable of increasing the realism of a video conference while including a virtual participant in the video conference image, and a non-transitory recording medium recording a program for executing the method.

BEST MODE

Figure 1:
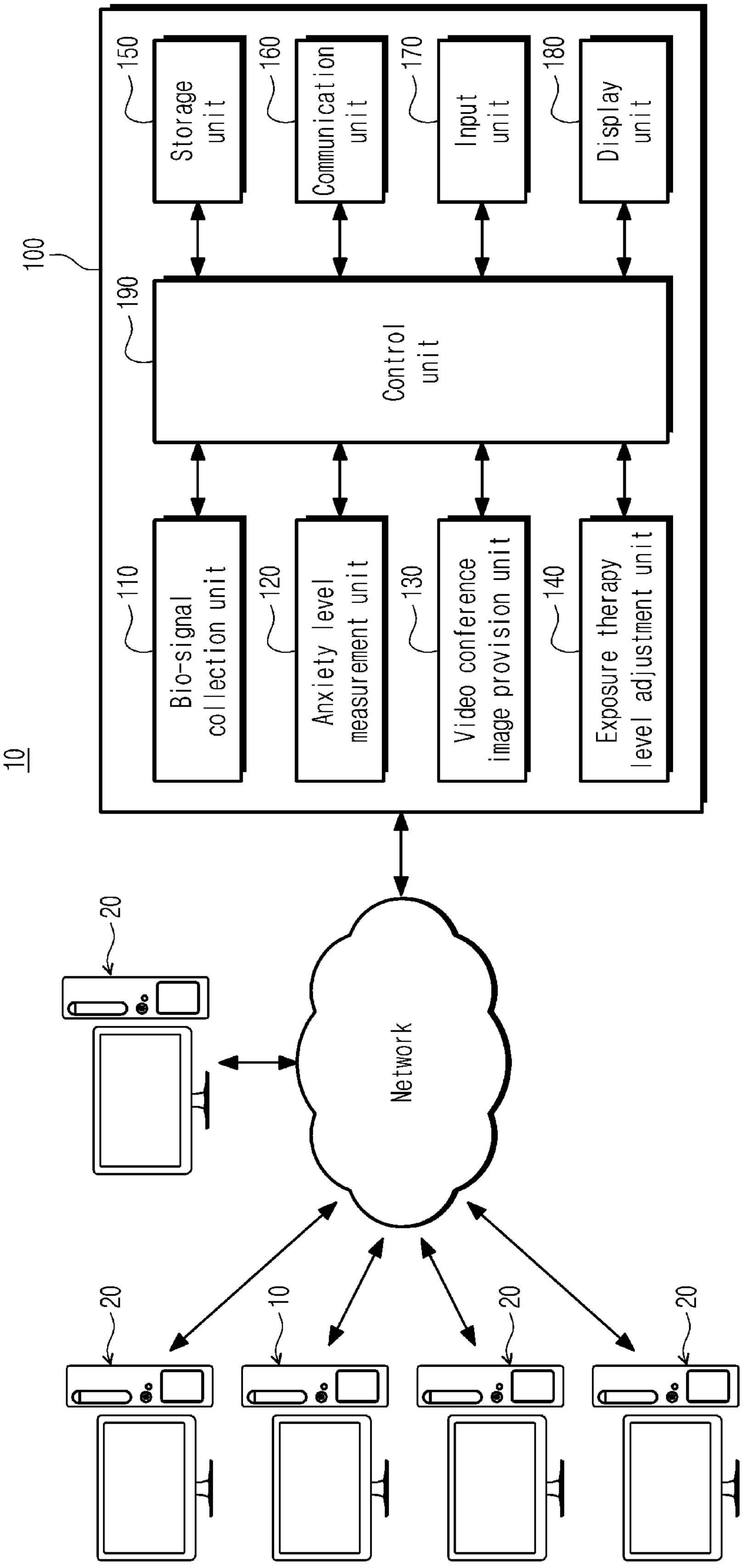
FIG. 1 is a block diagram of a video conference image-based social anxiety treatment system using biofeedback and exposure therapy, according to an embodiment of the inventive concept.

The above and other aspects, features and advantages of the inventive concept will become apparent from embodiments to be described in detail in conjunction with the accompanying drawings. However, the inventive concept is not limited to the embodiments disclosed below, but may be implemented in various forms. The embodiments of the inventive concept is provided to make the disclosure of the inventive concept complete and fully inform those skilled in the art to which the inventive concept pertains of the scope of the inventive concept. The same reference numerals denote the same elements throughout the specification.

In the specification, when a portion "comprises" a component, it will be understood that it may further include another component, without excluding other components unless specifically stated otherwise. As used herein, a "~unit" or "~part" may be a unit that processes at least one function or operation and may refer to, for example, a software, FPGA, or hardware component. The function provided by the "~unit" or "~part" may be performed separately by a plurality of components, or it may be integrated with other additional components. The "~unit" or "~part" of this specification may not be necessarily limited to software or hardware, and may be configured to be included in an addressable storage medium, or may be configured to operate one or more processors. Hereinafter, embodiments of the inventive concept will be described in detail with reference to the drawings.

FIG. 1 is a block diagram of a video conference image-based social anxiety treatment system using biofeedback and exposure therapy, according to an embodiment of the inventive concept. According to an embodiment of the inventive concept, the social anxiety treatment system 100 may be implemented as a server for treating social anxiety through exposure therapy in which a subject that is a target for social anxiety treatment performs a speech task through a non-face-to-face video conference with a large number of participants by communicating with a plurality of participant terminals 20 through a wired/wireless communication-based network.

The participant terminal 20 is a terminal used by the participant, and may be provided as, for example, a desktop PC, a laptop PC, a notebook PC, a smart phone, a smart pad, or the like, but is not limited thereto. One or more terminals among the plurality of participant terminals 20 may be user terminals 10 used by the subject. The participant terminal 20 may be provided as a terminal equipped with a communication interface and a camera capable of executing a video conference.

Referring to FIG. 1, according to an embodiment of the inventive concept, a video conference image-based social anxiety treatment system 100 using exposure therapy and biofeedback may include a bio-signal collection unit 110, an anxiety level measurement unit 120, a video conference image provision unit 130, an exposure therapy level adjustment unit 140, a storage unit 150, a communication unit 160, an input unit 170, a display unit 180, and a control unit 190.

While a subject to be treated for social anxiety performs a speech task through a video conference, the bio-signal collection unit 110 may collect a bio-signal of the subject. For example, the bio-signal of the subject collected by the bio-signal collection unit 110 may include a physiological signal such as heart rate variability (HRV), galvanic skin response (GSR), electrodermal activity (EDA), skin temperature, or the like. The bio-signal collection unit 110 may include a wearable terminal (e.g., a wireless wristband) configured to collect the subject's bio-signal while being worn on the subject.

While performing the speech task from the bio-signal of the subject collected by the bio-signal collection unit 110 while the speech task is performed, the anxiety level measurement unit 120 may include at least one processor configured to analyze the collected bio signal to measure an anxiety level of the subject in real time. The anxiety level measurement unit 120 may measure the subject's anxiety level by analyzing HRV, GSR, EDA, skin temperature, or the like through an algorithm. To determine whether there was a significant change by an algorithm, the anxiety level may be statistically compared with past data stored in a server and then biofeedback results may be provided to the subject.

Alternatively, instead of measuring an anxiety level based on a bio-signal of the subject collected by the bio-signal collection unit 110, the anxiety level measurement unit 120 may obtain a user image of the subject by using a camera, may analyze the facial expression and motion of the subject from the user image by an image analysis unit, and may measure the anxiety level of the subject.

In other words, the anxiety level measurement unit 120 may generate an image by capturing facial expressions and motions of the subject through a webcam and may analyze the corresponding image (e.g., a face image). Accordingly, even when a user does not wear a wearable terminal, the anxiety level measurement unit 120 may predict the user's anxiety level only with the obtained image of the user. In the case, the user's anxiety level may be measured by a deep learning-based artificial intelligence model (e.g., a convolutional artificial neural network model) that predicts a current state (e.g., an angry facial expression, a excited expression, an anxious facial expression, a fearful expression, a joyful expression, a sad expression, or the like) from the user's face image or motion.

The video conference image provision unit 130 may include a display and a program executable by a processor, wherein the program is configured to provide, via a user interface, the subject with a video conference image including a plurality of participants who access and participate in a video conference and a plurality of virtual participants thus previously prepared. Here, the participant may be a person who accesses the video conference in real time through the participant terminal 20 and actually participates in the video conference. The video conference image provision unit 130 may randomly and sequentially provide a plurality of real-time participant images and a plurality of first virtual participant images so as to simulate real-time access to the video conference when the subject is entered.

For example, the participant may be a person participating in a video conference while others are receiving social anxiety treatment, or a general video conference participant, to receive the opportunity to treat social anxiety, but a condition of the participant is not particularly limited thereto. The total number (the total number of participants including participants and virtual participants) of participants in the video conference image may be set variously, such as 2×2 or 3×3.

A subject receiving social anxiety treatment may perform a speech task after wearing a wristband for measuring physiological signals. During the speech task, shapes of participants participating in a non-face-to-face video conference and shapes of virtual participants may be provided in "m×n" form (each of 'm' and 'n' is an integer) on a screen of the subject. A level of a microphone volume, an exit button, and remaining speaking time may be displayed on the screen that the subject is capable of watching.

The topic of a speech task may include both selection and randomization elements. The topic of the speech task may be categorized as current affairs, self-introduction, opinion expression, and discussion. When a program is started, the subject may select one category, and a speech topic may be selected at random within the corresponding category. To this end, topics of various categories related to the speech task may be displayed on a terminal screen used by the subject.

When the subject selects one category from among the various categories of topics displayed on a screen to provide effective help to a user (subject) receiving exposure therapy for social anxiety symptoms, a sub-topic of the selected category may be selected randomly, and the randomly selected task may be presented in a form of a pop-up before the start of a programmatic video conference session. Accordingly, a speech task may be initiated on the corresponding topic. Sessions may be executed depending on a specified timetable, and a participant who is already entered and a participant who is being entered may be shown on a screen to enhance the sense of realism.

A virtual participant is not a person who accesses a video conference and actually participates in the video conference, but a person who takes a video assuming that the person is participating in the video conference with prior consent. At this time, virtual participant videos having various facial expressions may be prepared by taking videos of virtual participants while the virtual participants make various facial expressions (an angry facial expression, an indifferent facial expression, a bright facial expression, and the like).

Accordingly, the video conference image exposed such that a subject is capable of watching participants through the screen of the user terminal 10 may include face images (first face images) of a plurality of participants and face images of a plurality of virtual participants (second facial images). As such, while real participants and virtual participants, who do not actually participate in the video conference, but is incapable of being distinguished from a person who does not actually participate in by a subject, are mixed in the video conference, the inventive concept may provide the subject a video conference image. Accordingly, while the effectiveness of social anxiety treatment for the subject is increased by increasing the realism of the video conference, the social anxiety treatment level may be adjusted by adjusting the facial expression of the virtual participant image depending on an anxiety level of the subject.

The first face image (corresponding to a participant image) may include images of a plurality of real-time participants actually participating in the video conference through the participant terminal 20. The second face image (corresponding to a virtual participant image) may include a plurality of virtual participant images having different facial expressions and anxiety-inducing levels. A plurality of virtual participant images may include a plurality of previously obtained videos of a plurality of virtual participants having anxious facial expressions, indifferent facial expressions, and bright facial expressions.

The virtual participant image may be an upper body image of a single object recorded with consent for the purpose of inducing an emotional response. These virtual participant images may be evaluated and edited to determine whether there is an actual emotional reaction-inducing effect, and then may be stored in advance on a server. Besides, the anxiety-inducing level of each virtual participant image may be evaluated in advance through a likert scale. The anxiety-inducing level evaluated for each virtual participant image may be stored in the server together with the virtual participant image.

The exposure therapy level adjustment unit 140 may include one or more processors configured to adjust an exposure therapy level based on the measured anxiety level of the subject that changes according to the video conference image. In other words, while the subject is performing the speech task through a video conference, the subject's anxiety level may be measured in real time. Accordingly, the level of exposure therapy given to the subject by the exposure therapy level adjustment unit 140 may be adjusted depending on a change in anxiety level of the measured subject.

At this time, the exposure therapy level adjustment unit 140 may adjust an exposure rate of the first face image or the expression of the second face image, depending on the anxiety level of the subject. In an embodiment, the exposure therapy level adjustment unit 140 may adjust exposure ratios of a plurality of virtual participant images depending on the subject's anxiety level, virtual participant's expression change or virtual participant's replacement, or the like.

For example, when the anxiety level compared to a previous session has decreased to a first reference anxiety level or less while the subject is performing a speech task at a video conference, the exposure therapy level adjustment unit 140 may increase a stimulus frequency and/or stimulus intensity that causes anxiety in a subject in the video conference image to increase the effect of exposure therapy on the subject. In this case, for example, the exposure therapy level adjustment unit 140 may switch an image of at least one virtual participant among a plurality of virtual participant images being exposed in the video conference image from a bright facial expression to an indifferent facial expression or an angry facial expression or may switch an image of the virtual participant from an indifferent facial expression to an angry facial expression.

On the other hand, when the anxiety level compared to the existing session increases to be greater than or equal to a second reference anxiety level higher than the first reference anxiety level while the subject is performing the speech task, the exposure therapy level adjustment unit 140 may increase the frequency of neutral stimuli and may decrease the frequency and intensity of anxiety stimuli. In this case, for example, the exposure therapy level adjustment unit 140 may switch an image of at least one virtual participant among a plurality of virtual participant images being exposed in the video conference image from an indifferent facial expression to a bright facial expression or may switch the image from an angry facial expression to a bright facial expression.

In addition, the exposure therapy level adjustment unit 140 may adjust the anxiety level applied to the subject through replacement of a virtual participant exposed to the video conference image. For example, the exposure therapy level adjustment unit 140 may allow a virtual participant with a bright facial expression to leave from the video conference, and then may allow a virtual participant with an indifferent facial expression or an angry facial expression to enter the video conference, thereby increasing the anxiety level exposed to the subject. Alternatively, the exposure therapy level adjustment unit 140 may allow a virtual participant with an angry facial expression to leave from the video conference, and then may allow a virtual participant with a bright or indifferent facial expression to enter the video conference, thereby decreasing the anxiety level exposed to the subject.

In another embodiment of the inventive concept, the exposure therapy level adjustment unit 140 may provide a participant terminal with a guide phrase for changing a participant's facial expression depending on the subject's anxiety level. For example, when the anxiety level compared to the previous session has decreased to a first reference anxiety level or less while the subject is performing a speech task at a video conference, the exposure therapy level adjustment unit 140 may find at least one participant with a relatively bright or indifferent facial expression, and then may display a guide phrase that induces a change in facial expression, such as "please make an indifferent facial expression (or an angry facial expression)," to the corresponding participant terminal 20. Accordingly, when the corresponding participant changes a facial expression to an indifferent or angry facial expression, the level of anxiety (stimulus frequency and/or stimulus intensity that induces anxiety in the subject) applied to the subject may increase.

On the other hand, when the anxiety level compared to the previous session has increased to a second reference anxiety level or higher while the subject is performing a speech task at a video conference, the exposure therapy level adjustment unit 140 may find at least one participant with an indifferent facial expression or an angry facial expression, and then may display a guide phrase that induces a change in facial expression, such as "please make a bright facial expression (or an indifferent facial expression)," to the corresponding participant terminal 20. Accordingly, when the corresponding participant changes a facial expression to a bright or indifferent facial expression, the level of anxiety (stimulus frequency and/or stimulus intensity that induces anxiety in the subject) applied to the subject may decrease.

The storage unit 150 may store a program for providing a social anxiety treatment function through a video conference, a previously prepared video of a virtual participant, and various other pieces of information. The storage unit 150 may be implemented with various memories such as ROM, RAM, flash memory, and the like and is not limited to the memory described above. The communication unit 160 may communicate with the participant terminal 20 through a wired/wireless communication interface. The communication unit 160 may transmit and receive data for a video conference through wired communication (e.g., wired LAN), Wi-Fi, Bluetooth, LTE, and the like.

The input unit 170 may be provided as an input interface (e.g., a keyboard, a mouse, a touchpad, an electronic pen, or the like) for inputting a command to execute a social anxiety treatment program through a video conference. The display unit 180 may provide a function of displaying a video conference image on screens of a plurality of the participant terminals 20. The control unit 190 may include at least one processor that executes a program for social anxiety treatment and controls each component of the social anxiety treatment system 100.

As described above, the social anxiety treatment system according to an embodiment of the inventive concept may allow a participant to conveniently receive a social anxiety treatment service by downloading and executing an app. Alternatively, a medical professional may execute a program through a medical terminal, and then the social anxiety treatment system according to an embodiment of the inventive concept may provide the social anxiety treatment service. In this case, the user terminal 10 used by the subject may be integrated with the social anxiety treatment system so as to be provided or may be implemented as a medical terminal used by a medical institution.

Figure 2:
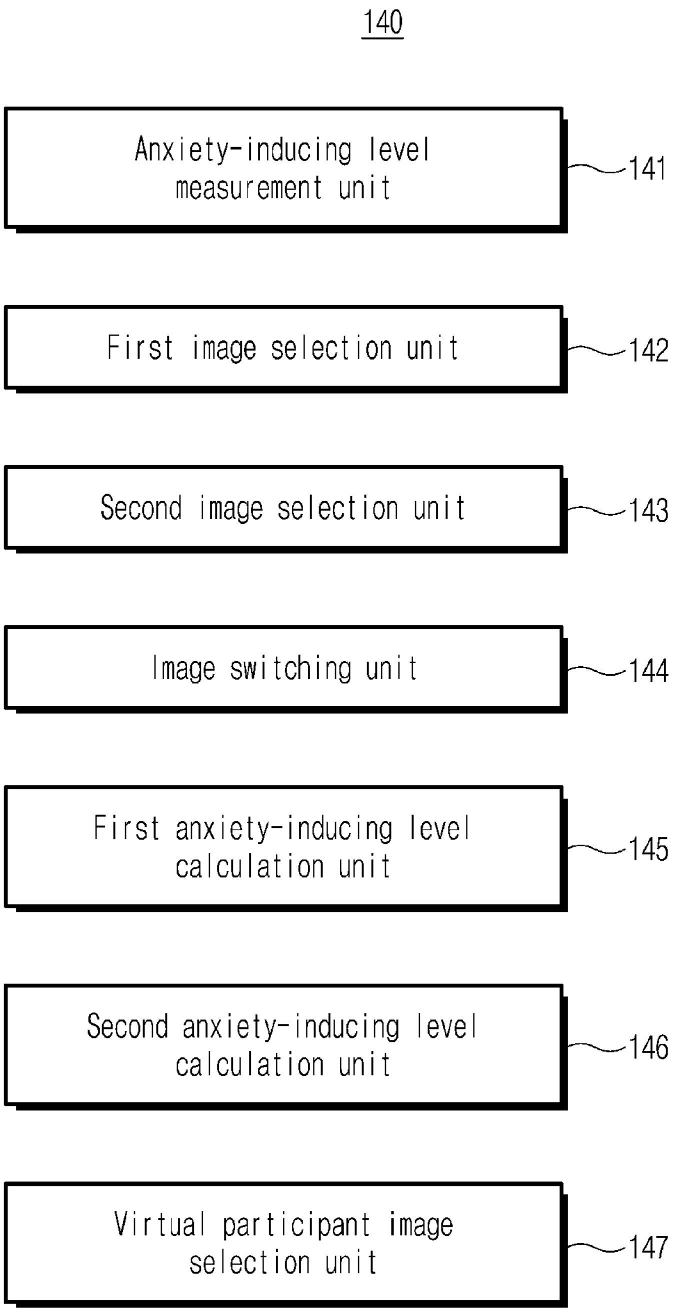
FIG. 2 is a block diagram of an exposure therapy level adjustment unit constituting a video conference image-based social anxiety treatment system using biofeedback and exposure therapy, according to an embodiment of the inventive concept.

FIG. 2 is a block diagram of an exposure therapy level adjustment unit constituting a video conference image-based social anxiety treatment system using biofeedback and exposure therapy, according to an embodiment of the inventive concept. Referring to FIG. 2, the exposure therapy level adjustment unit 140 may include an anxiety-inducing level measurement unit 141, a first image selection unit 142, a second image selection unit 143, an image switching unit 144, a first anxiety-inducing level calculation unit 145, a second anxiety-inducing level calculation unit 146, and a virtual participant image selection unit 147.

Figure 3:
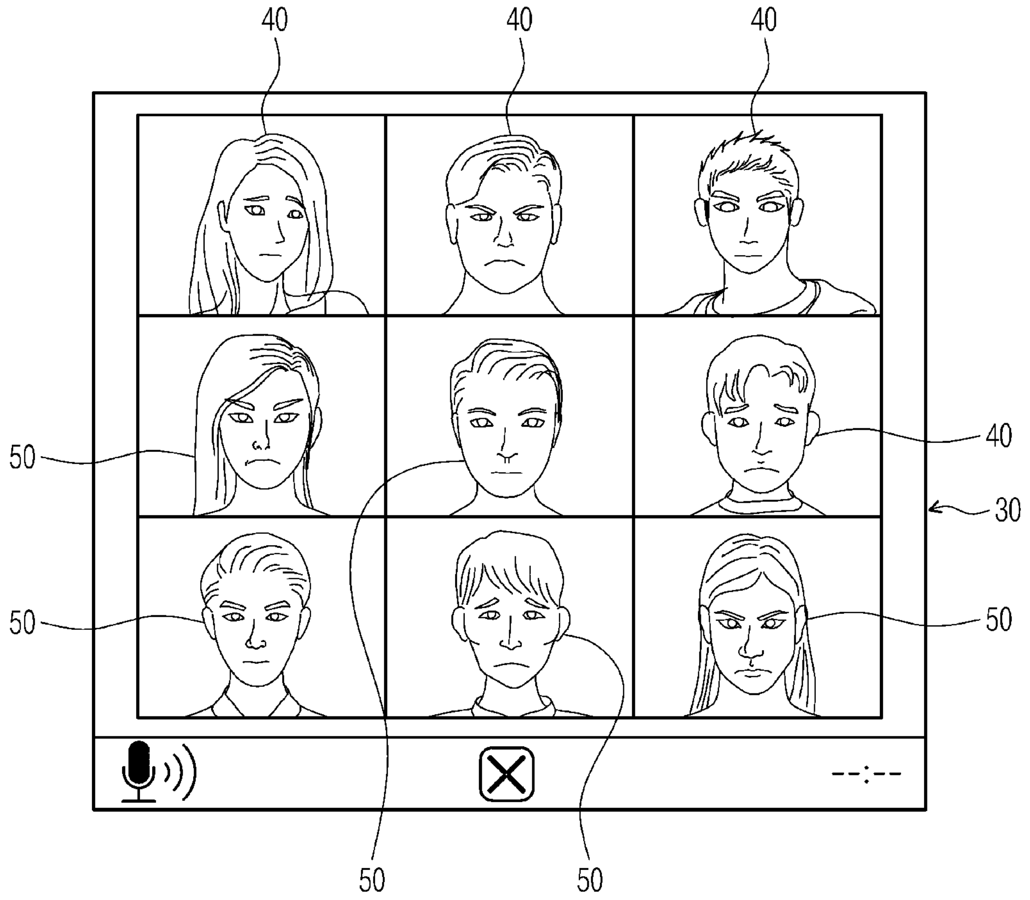
FIGS. 3 to 5 are diagrams for describing functions of a video conference image-based social anxiety treatment system using biofeedback and exposure therapy, according to an embodiment of the inventive concept.
Figure 4:
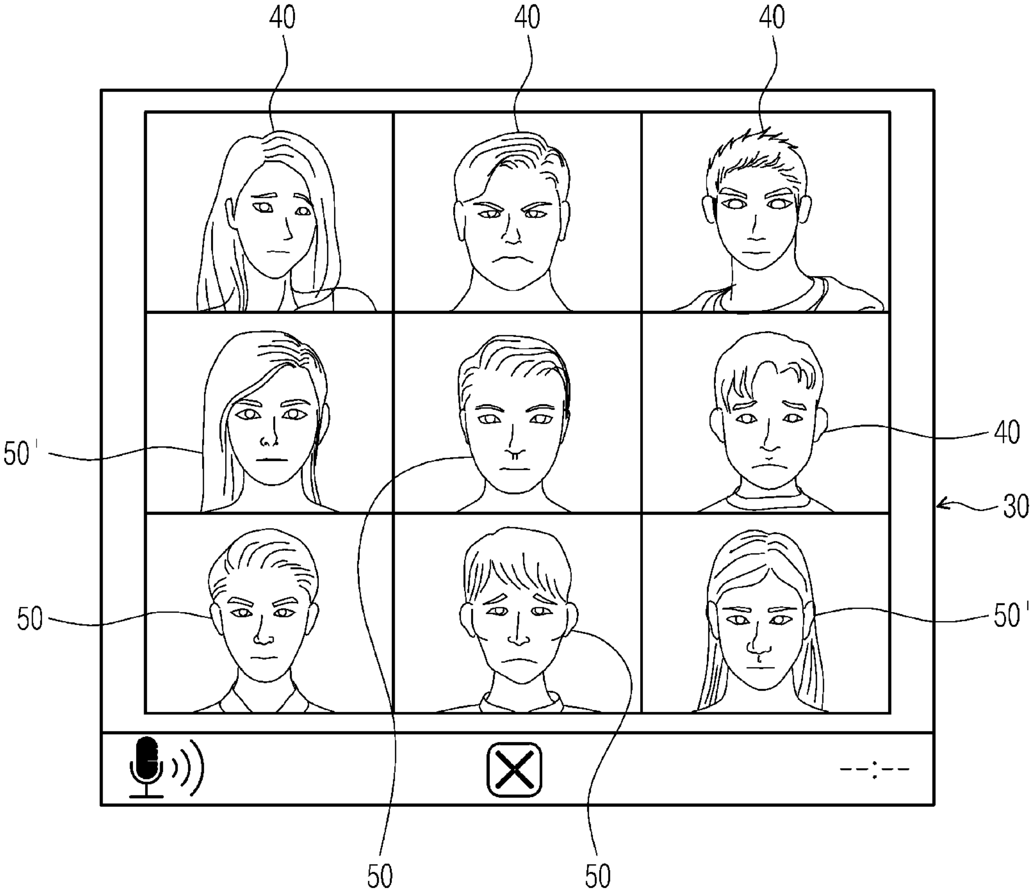
Figure 5:
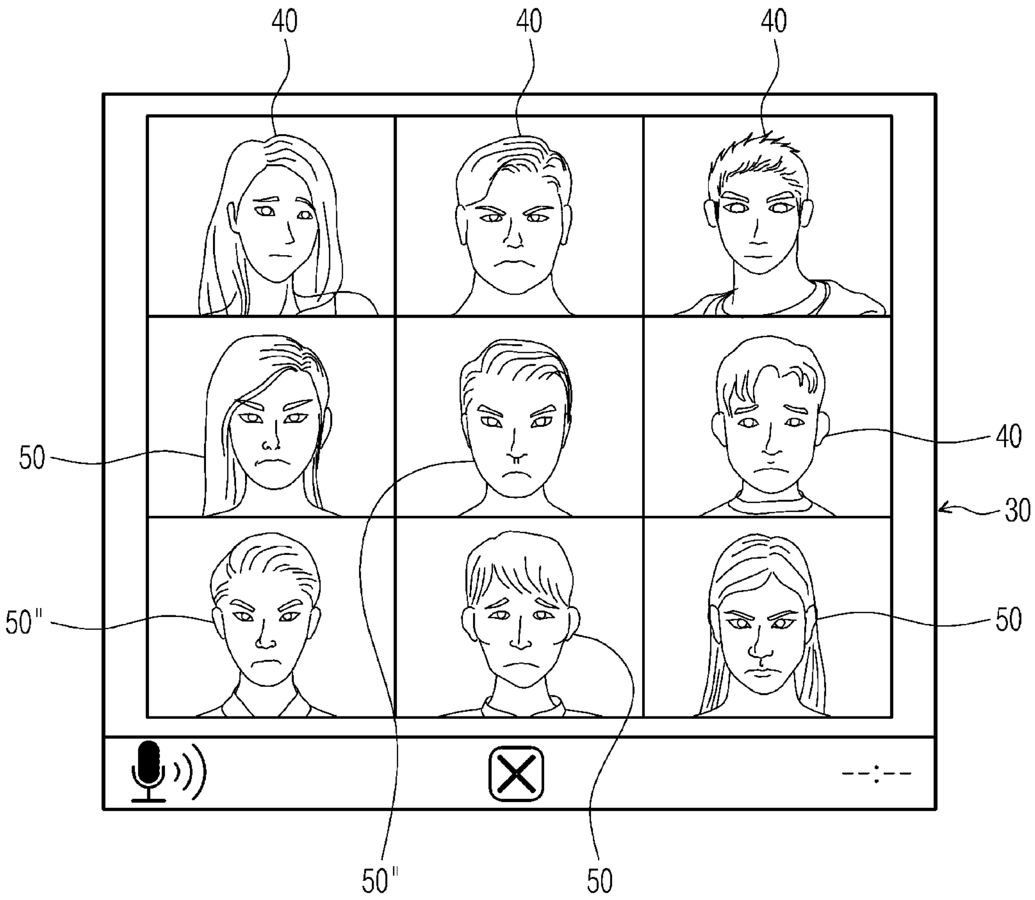

FIGS. 3 to 5 are diagrams for describing functions of a video conference image-based social anxiety treatment system using biofeedback and exposure therapy, according to an embodiment of the inventive concept. FIG. 3 is a diagram illustrating a video conference image being currently displayed to a subject. FIG. 4 is a diagram illustrating that some of virtual participant images among the video conference images shown in FIG. 3 are switched from an image of an angry facial expression to an image of an indifferent facial expression. FIG. 5 is a diagram illustrating that some of virtual participant images among the video conference images shown in FIG. 3 are switched from an image of an indifferent facial expression to an image of an angry facial expression.

Referring to FIGS. 2 to 5, the anxiety-inducing level measurement unit 141 may measure an anxiety-inducing level of each participant's facial expression from a plurality of real-time participant images 40 exposed to a subject through a video conference image 30. The participant's anxiety-inducing level may be measured by a deep learning-based artificial intelligence model (e.g., a convolution artificial neural network model) that predicts an emotional state (an angry facial expression, an indifferent facial expression, a bright facial expression, or the like) from a person's face image, and a detailed description of the artificial intelligence model will be omitted such that the gist of the inventive concept is not obscured. The anxiety-inducing level of the virtual participant video may be set in advance or measured in real time by an artificial intelligence model.

The first image selection unit 142 may select at least one first image (an image that is currently displayed in a video conference image, but is to be replaced with another image) from among a plurality of real-time participant images 40 and a plurality of first virtual participant images 50 based on the anxiety-inducing level from measuring each of the plurality of real-time participant images and the anxiety-inducing level of each of the plurality of first virtual participant images 50 being exposed to the subject through the video conference.

For example, when the current anxiety level of a subject performing a speech task in a video conference is low, it is necessary to induce stronger anxiety in the subject. In this case, to increase the effect of strengthening anxiety through video replacement, the first image selection unit 142 may select one or more first images in order of lowest anxiety-inducing level among the plurality of participant images 40 and the plurality of first virtual participant images 50 currently being exposed during the video conference.

On the other hand, when the current anxiety level of a subject performing a speech task in the video conference is excessively high, it is necessary to reduce the anxiety applied to the subject. In this case, to increase the effect of relaxing anxiety through video replacement, the first image selection unit 142 may select one or more first images in order of lowest anxiety-inducing level among the plurality of participant images 40 and the plurality of first virtual participant images 50 currently being exposed during the video conference.

Moreover, together with the anxiety-inducing levels of the participant image 40 and the first virtual participant image 50, the first image selection unit 142 may select one or more first images in consideration of an image display location where the corresponding participant image 40 and the first virtual participant image 50 are displayed in a video conference image. For example, when the subject's anxiety level is relatively far out of the reference anxiety level range, the first image selection unit 142 may select a first image by applying a high score to the participant image 40 or the first virtual participant image (50), which is displayed at a first image display location (e.g., a preset first screen location such as a central area of a screen) most conspicuous by the subject for effective increase and decrease in an anxiety level.

On the other hand, when the subject's anxiety level does not deviate relatively far from a reference anxiety level range, the first image selection unit 142 may select the first image by applying a high score to the participant image 40 or the virtual participant image 50, which is displayed at a second image display location (e.g., a preset second screen location such as a screen corner area) that is not conspicuous by the subject, to slightly increase or decrease the anxiety level.

The second image selection unit 143 may select at least one second image (an image that is not currently being displayed in a video conference image, but will be displayed in the video conference image obtained by replacing the first image) among a plurality of second virtual participant images, which are not exposed to the subject through the video conference, based on the real-time anxiety level of the subject performing the speech task in the video conference.

For example, when the current anxiety level of the subject performing the speech task in the video conference is low, the second image selection unit 143 may select one or more second images in order of highest anxiety-inducing level among a plurality of second virtual participant images that are not exposed to the subject through the video conference so as to cause more anxiety in the subject. In the case, the number of second images selected by the second image selection unit 143 may be the same as the number of first images selected by the first image selection unit 142.

As another example, when the current anxiety level of the subject performing the speech task in the video conference is excessively high, the second image selection unit 143 may select one or more second images in order of lowest anxiety-inducing level among a plurality of second virtual participant images exposed to the subject through the video conference so as to reduce the anxiety applied to the subject.

The image switching unit 144 may switch a first image (an image selected by a first image selection unit), which is being exposed to the subject through the video conference, to a second image 50' or 50" selected by the second image selection unit 143 and then may expose the second image 50' or 50" to the subject through the video conference image 30 instead of the first image. When switching a plurality of first images to the plurality of second images 50' or 50" so as to simulate a real-time connection to a video conference, the image switching unit 144 may randomly and sequentially switch the plurality of first images into the plurality of second images 50' or 50".

In other words, when switching the plurality of first images to the plurality of second images 50' or 50", the image switching unit 144 may allow the subject to perceive that a participant participating in a video conference naturally exits and then a new participant participates in the video conference, by sequentially switching the plurality of first images to the plurality of second images 50' or 50" at time intervals thus set or arbitrarily determined.

In an embodiment of the inventive concept, while the anxiety level of the subject performing the speech task in the video conference remains within a specific range and does not deviate from the corresponding range, the anxiety level delivered to the subject may not change due to a change in facial expressions of participants participating in the video conference in real time, under control of the first anxiety-inducing level calculation unit 145, the second anxiety-inducing level calculation unit 146 and the virtual participant image selection unit 147.

The first anxiety-inducing level calculation unit 145 may calculate a first anxiety-inducing level by summing anxiety-inducing levels from respectively measuring a plurality of real-time participant images. As previously described, the anxiety-inducing level of each participant image may be measured by an artificial intelligence model. The first anxiety-inducing level calculation unit 145 may calculate the first anxiety-inducing level in real time by summing the anxiety-inducing levels of all participant images, and may periodically calculate a first change amount of the first anxiety-inducing level during a set time (e.g., several seconds to several minutes).

The second anxiety-inducing level calculation unit 146 may calculate the second anxiety-inducing level by summing the anxiety-inducing levels from respectively measuring a plurality of first virtual participant images being displayed in a video conference image. The second anxiety-inducing level calculation unit 146 may calculate the second anxiety-inducing level in real time by summing the anxiety-inducing levels of all participant images being displayed in a video conference image, and may periodically calculate a second change amount of the second anxiety-inducing level during a set time (e.g., several seconds to several minutes).

The virtual participant image selection unit 147 may select a plurality of first virtual participant images from among a plurality of virtual participant images such that a second change amount of the second anxiety-inducing level calculated by the second anxiety-inducing level calculation unit 146 offsets a first change amount of the first anxiety-inducing level calculated by the first anxiety-inducing level calculation unit 145. Accordingly, while the subject's anxiety level is maintained at a specific level, anxiety-inducing levels of all real-time participant images and virtual participant images displayed in the video conference image are capable of being maintained at a specific level, thereby preventing a change in the anxiety-inducing level applied to the subject due to a change in the participant's facial expression in real time.

For example, when a participant participating in real-time changes from a bright facial expression to a dark facial expression, the virtual participant image selection unit 147 may switch a virtual participant image with a dark facial expression displayed in a video conference into a new virtual participant image with a bright facial expression. On the other hand, when a participant participating in real-time changes from a dark facial expression to a bright facial expression, the virtual participant image selection unit 147 may switch a virtual participant image with a bright facial expression displayed in a video conference into a new virtual participant image with a dark facial expression.

Figure 6:
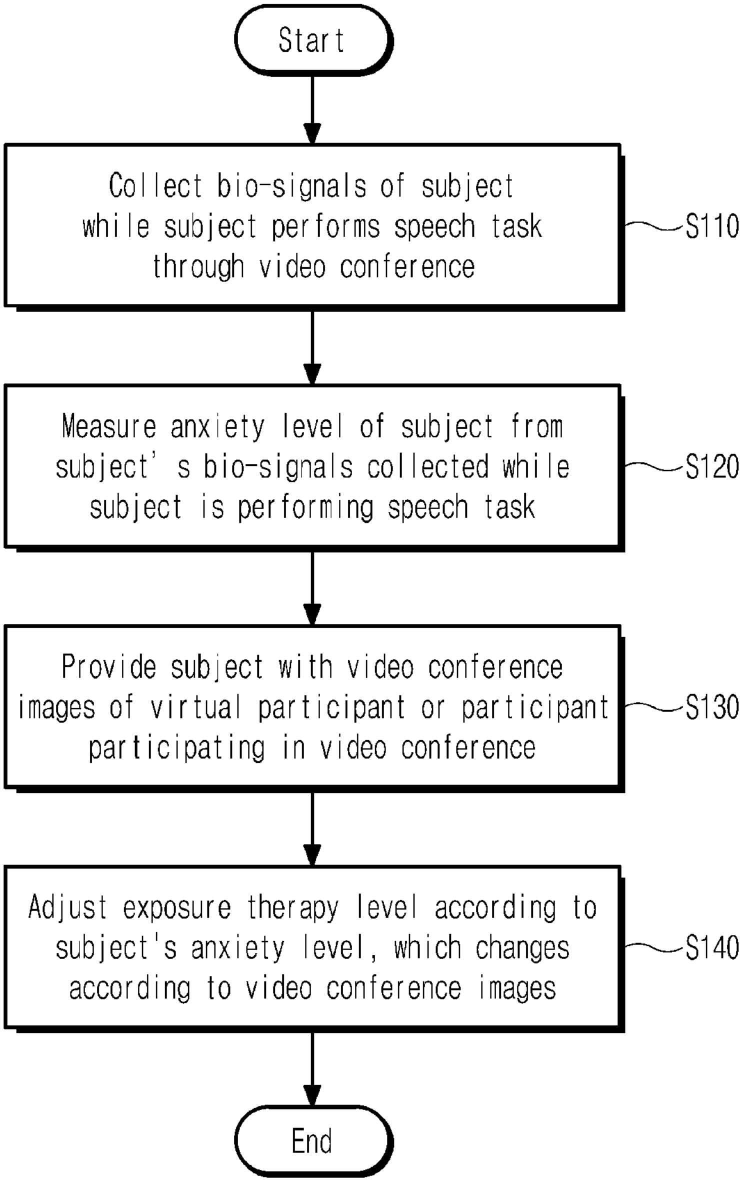
FIG. 6 is a flowchart of a video conference image-based social anxiety treatment method using biofeedback and exposure therapy that is executed by a program recorded on a recording medium, according to an embodiment of the inventive concept.
Figure 7:
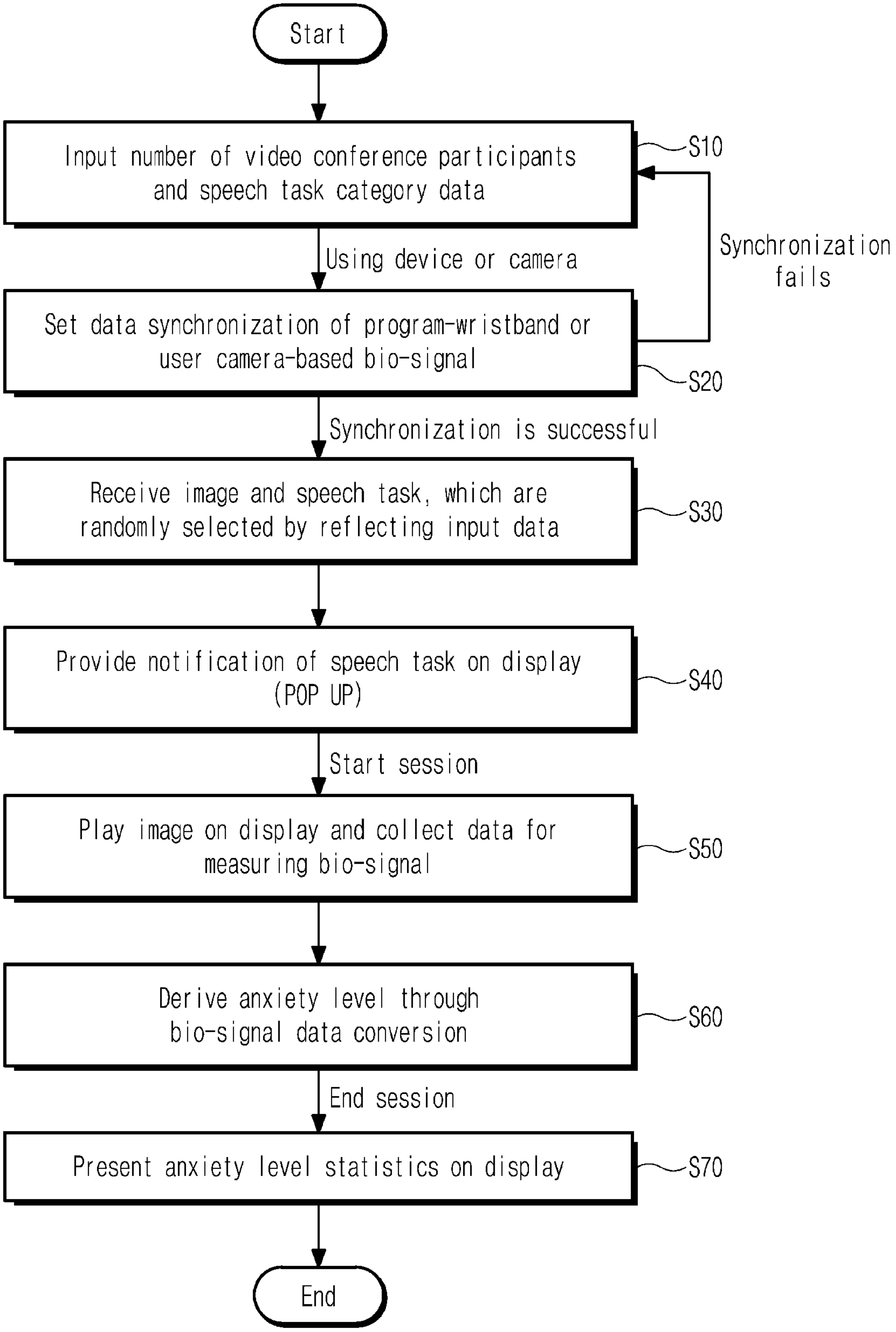
FIG. 7 is a flowchart showing the social anxiety treatment method of FIG. 6 in more detail.

FIG. 6 is a flowchart of a video conference image-based social anxiety treatment method using biofeedback and exposure therapy that is executed by a program recorded on a recording medium, according to an embodiment of the inventive concept. FIG. 7 is a flowchart showing the social anxiety treatment method of FIG. 6 in more detail. Referring to FIGS. 1, 6, and 7, a subject, a medical expert, or a server manager may input the number of video conference participants and speech task category data (S10). The number of video conference participants or the speech task category data may be set by default.

When the subject wears a wearable device (a wearable terminal) such as a wristband for measuring a bio-signal, the subject may set data synchronization with the wristband (S20). Alternatively, while the subject does not have a wearable terminal, the bio-signal may be collected by a camera, which obtains an image by photographing a speech task performance state of the subject, and an image analysis unit that measures the bio-signal of the subject by analyzing an image obtained by the camera. When data synchronization of the wearable terminal and/or camera is successful, an image and a speech task, which are randomly selected by reflecting the input data, are received (S30). In the case, topics of various categories related to the speech task may be displayed on a terminal screen used by the subject.

When the subject selects one category from among the various categories of topics displayed on a screen to provide effective help to a user (subject) receiving exposure therapy for social anxiety symptoms, a sub-topic of the selected category may be selected randomly. The randomly selected task may be presented in a form of a pop-up before the start of a programmatic video conference session. Accordingly, the speech task for the corresponding topic may be displayed and the speech task may be started (S40). When the speech task is started, the video conference image is played on a screen of a user terminal, and, data related to the subject's bio-signal is simultaneously collected by using a wearable terminal and/or a camera image analysis (S50).

In operation S50, while the subject that is a target of social anxiety treatment is performing the speech task through a video conference, the bio-signal collection unit 110 may collect the bio-signal of the subject by using a wearable terminal and/or a camera image analysis (S110). For example, the bio-signal of the subject collected by the bio-signal collection unit 110 may include physiological signals (e.g., HRV, GSR, EDA, a skin temperature, and the like) and facial expressions/actions related to the user's anxiety level analyzed from the user image, and the like.

In operation S60, while performing the speech task from the bio-signal of the subject collected by the bio-signal collection unit 110 while the speech task is performed, the anxiety level measurement unit 120 may measure an anxiety level of the subject in real time (S120). The anxiety level measurement unit 120 may measure the subject's anxiety level by analyzing HRV, GSR, EDA, skin temperature, or the like through an algorithm. The anxiety level measurement unit 120 may measure the anxiety level of the subject through camera image analysis without using the bio-signal collection unit 110. In operation S70, to determine whether there was a significant change by an algorithm, the anxiety level may be statistically compared with past data stored in a server and then biofeedback results may be provided to the subject.

The video conference image provision unit 130 may provide the subject with a video conference image including a plurality of participants who access and participate in a video conference and a plurality of virtual participants thus previously prepared (S130). Here, the participant may be a person who accesses the video conference in real time through the participant terminal 20 and actually participates in the video conference. The video conference image provision unit 130 may randomly and sequentially provide a plurality of real-time participant images and a plurality of first virtual participant images so as to simulate real-time access to the video conference when the subject is entered.

The video conference image exposed such that a subject is capable of watching participants through the screen of the user terminal 10 may include face images (first face images) of a plurality of participants and face images of a plurality of virtual participants (second facial images). While real participants and virtual participants, who do not actually participate in the video conference, but is incapable of being distinguished from a person who does not actually participate in by a subject, are mixed in the video conference, the inventive concept may provide the subject a video conference image. Accordingly, while the effectiveness of social anxiety treatment for the subject is increased by increasing the realism of the video conference, the social anxiety treatment level may be adjusted by adjusting the facial expression of the virtual participant image depending on an anxiety level of the subject.

The first face image (corresponding to a participant image) may include images of a plurality of real-time participants actually participating in the video conference through the participant terminal 20. The second face image (corresponding to a virtual participant image) may include a plurality of virtual participant images having different facial expressions and anxiety-inducing levels. A plurality of virtual participant images may include a plurality of previously obtained videos of a plurality of virtual participants having anxious facial expressions, indifferent facial expressions, and bright facial expressions.

The virtual participant image may be an upper body image of a single object recorded with consent for the purpose of inducing an emotional response. These virtual participant images may be evaluated and edited to determine whether there is an actual emotional reaction-inducing effect, and then may be stored in advance on a server. Besides, the anxiety-inducing level of each virtual participant image may be evaluated in advance through a Likert scale. The anxiety-inducing level evaluated for each virtual participant image may be stored in the server together with the virtual participant image.

The exposure therapy level adjustment unit 140 may adjust an exposure therapy level depending on the anxiety level of the subject that changes according to the video conference image (S140). While the subject is performing the speech task through a video conference, the exposure therapy level adjustment unit 140 may adjust the level of exposure therapy given to the subject depending on a change in anxiety level of the measured subject by measuring the subject's anxiety level in real time.

The exposure therapy level adjustment unit 140 may adjust an exposure rate of the first face image or the expression of the second face image, depending on the anxiety level of the subject. In an embodiment, the exposure therapy level adjustment unit 140 may adjust exposure ratios of a plurality of virtual participant images depending on the subject's anxiety level, virtual participant's expression change or virtual participant's replacement, or the like.

For example, when the anxiety level compared to a previous session has decreased to a first reference anxiety level or less while the subject is performing a speech task at a video conference, the exposure therapy level adjustment unit 140 may increase a stimulus frequency and/or stimulus intensity that causes anxiety in a subject in the video conference image to increase the effect of exposure therapy on the subject.

On the other hand, when the anxiety level compared to the existing session increases to be greater than or equal to a second reference anxiety level higher than the first reference anxiety level while the subject is performing the speech task, the exposure therapy level adjustment unit 140 may increase the frequency of neutral stimuli and may decrease the frequency and intensity of anxiety stimuli.

In addition, the exposure therapy level adjustment unit 140 may adjust the anxiety level applied to the subject through replacement of a virtual participant exposed to the video conference image. In another embodiment of the inventive concept, the exposure therapy level adjustment unit 140 may provide a participant terminal with a guide phrase for changing a participant's facial expression depending on the subject's anxiety level.

Figure 8:
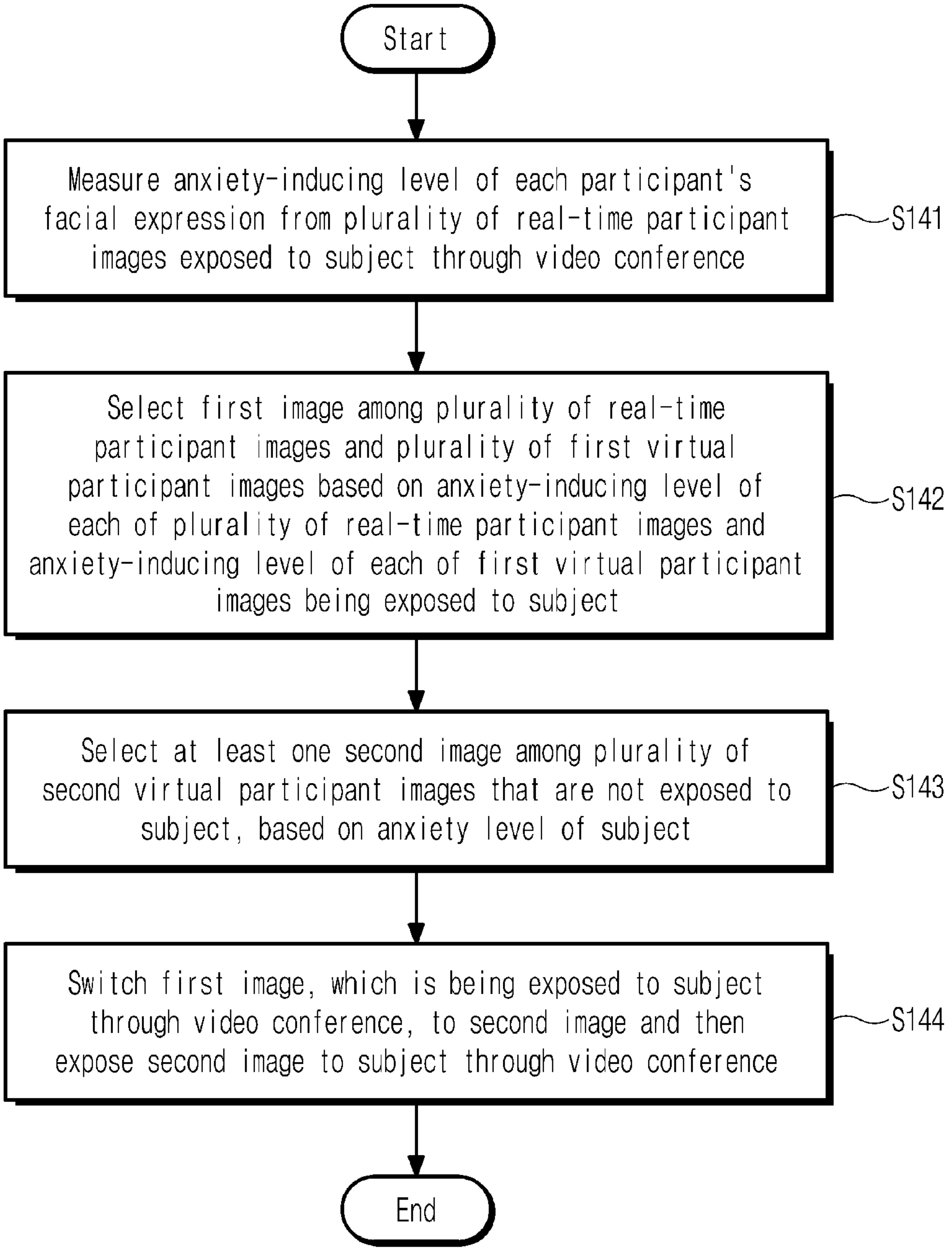
FIG. 8 is a flowchart illustrating an embodiment of operation S140 of FIG. 6 in detail.

FIG. 8 is a flowchart illustrating an embodiment of operation S140 of FIG. 6 in detail. Referring to FIGS. 2 to 6 and 8, the anxiety-inducing level measurement unit 141 may measure an anxiety-inducing level of each participant's facial expression from the plurality of real-time participant images 40 exposed to a subject through a video conference image 30 (S141).

The participant's anxiety-inducing level may be measured by a deep learning-based artificial intelligence model (e.g., a convolution artificial neural network model) that predicts an emotional state (an angry facial expression, an indifferent facial expression, a bright facial expression, or the like) from a person's face image. The anxiety-inducing level of the virtual participant video may be set in advance or measured in real time by an artificial intelligence model.

The first image selection unit 142 may select at least one first image (an image that is currently displayed in a video conference image, but is to be replaced with another image) among a plurality of real-time participant images 40 and a plurality of first virtual participant images 50 based on the anxiety-inducing level from measuring each of the plurality of real-time participant images and the anxiety-inducing level of each of the plurality of first virtual participant images 50 being exposed to the subject through the video conference (S142).

Moreover, together with the anxiety-inducing levels of the participant image 40 and the first virtual participant image 50, the first image selection unit 142 may select one or more first images in consideration of an image display location where the corresponding participant image 40 and the first virtual participant image 50 are displayed in a video conference image.

The second image selection unit 143 may select at least one second image (an image that is not currently being displayed in a video conference image, but will be displayed in the video conference image obtained by replacing the first image) among a plurality of second virtual participant images, which are not exposed to the subject through the video conference, based on the real-time anxiety level of the subject performing the speech task in the video conference (S143).

The image switching unit 144 may switch a first image (an image selected by a first image selection unit), which is being exposed to the subject through the video conference, to a second image 50' or 50" selected by the second image selection unit 143 and then may expose the second image 50' or 50" to the subject through the video conference image 30 instead of the first image (S144). In this case, when switching a plurality of first images to the plurality of second images 50' or 50" so as to simulate a real-time connection to a video conference, the image switching unit 144 may randomly and sequentially switch the plurality of first images into the plurality of second images 50' or 50".

Figure 9:
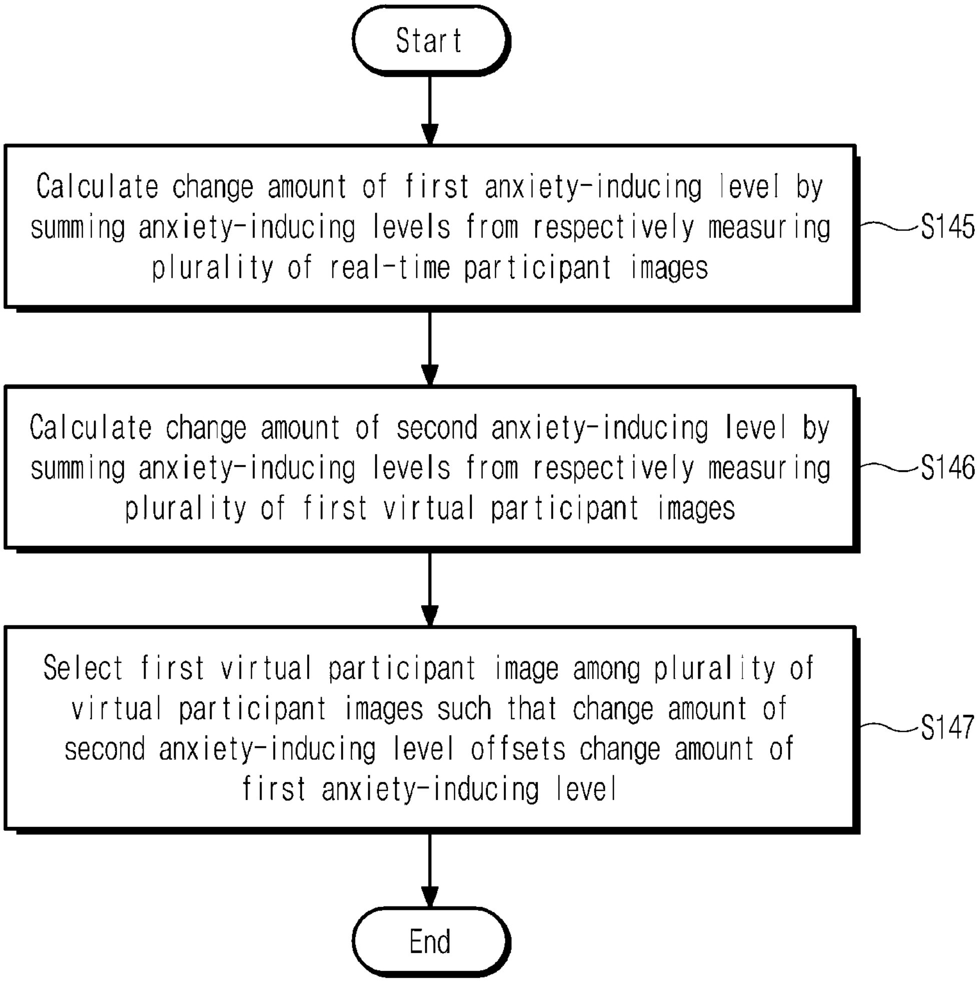
FIG. 9 is a flowchart illustrating another embodiment of operation S140 of FIG. 6 in detail.

FIG. 9 is a flowchart illustrating another embodiment of operation S140 of FIG. 6 in detail. Referring to FIGS. 2 to 6 and 9, the first anxiety-inducing level calculation unit 145 may calculate a first anxiety-inducing level by summing anxiety-inducing levels from respectively measuring a plurality of real-time participant images (S145). The first anxiety-inducing level calculation unit 145 may calculate the first anxiety-inducing level in real time by summing the anxiety-inducing levels of all participant images, and may periodically calculate a first change amount of the first anxiety-inducing level during a set time (e.g., several seconds to several minutes).

The second anxiety-inducing level calculation unit 146 may calculate the second anxiety-inducing level by summing the anxiety-inducing levels from respectively measuring a plurality of first virtual participant images being displayed in a video conference image (S146). The second anxiety-inducing level calculation unit 146 may calculate the second anxiety-inducing level in real time by summing the anxiety-inducing levels of all participant images being displayed in a video conference image, and may periodically calculate a second change amount of the second anxiety-inducing level during a set time (e.g., several seconds to several minutes).

The virtual participant image selection unit 147 may select a plurality of first virtual participant images from among a plurality of virtual participant images such that a second change amount of the second anxiety-inducing level calculated by the second anxiety-inducing level calculation unit 146 offsets a first change amount of the first anxiety-inducing level calculated by the first anxiety-inducing level calculation unit 145 (S147). Accordingly, while the subject's anxiety level is maintained at a specific level, anxiety-inducing levels of all real-time participant images and virtual participant images displayed in the video conference image are capable of being maintained at a specific level, thereby preventing a change in the anxiety-inducing level applied to the subject due to a change in the participant's facial expression in real time.

The above-described embodiments may be implemented with hardware components, software components, and/or a combination of hardware components and software components. For example, the devices, methods, and elements described in the embodiments of the inventive concept may be implemented by using one or more general-use computers or special-purpose computers, such as a processor, a controller, an arithmetic logic unit (ALU), a digital signal processor, a microcomputer, a field programmable array (FPA), a programmable logic unit (PLU), a microprocessor, or any device which may execute instructions and respond.

A processing unit may perform an operating system (OS) or one or software applications running on the OS. Further, the processing unit may access, store, manipulate, process and generate data in response to execution of software. It will be understood by those skilled in the art that although a single processing unit may be illustrated for convenience of understanding, the processing unit may include a plurality of processing elements and/or a plurality of types of processing elements.

For example, the processing unit may include a plurality of processors or one processor and one controller. Also, the processing unit may have a different processing configuration, such as a parallel processor. Software may include computer programs, codes, instructions or one or more combinations thereof and configure a processing unit to operate in a desired manner or independently or collectively control the processing unit.

Software and/or data may be embodied in any type of machine, components, physical equipment, virtual equipment, computer storage media or devices so as to be interpreted by the processing unit or to provide instructions or data to the processing unit. Software may be dispersed throughout computer systems connected via networks and be stored or executed in a dispersion manner. Software and data may be recorded in one or more computer-readable storage media.

The methods according to the above-described embodiments may be recorded in a computer-readable medium including program instructions that are executable through various computer devices. The non-transitory computer-readable medium may include program instructions, data files, data structures, etc. independently or may include a combination thereof. The program instructions recorded in the media may be designed and configured specially for the exemplary embodiments of the inventive concept or be known and available to those skilled in computer software.

The computer-readable medium may include a hardware device, which is specially configured to store and execute program instructions, such as magnetic media (e.g., a hard disk drive, a floppy disk, and a magnetic tape), optical media (e.g., CD-ROM and DVD), read only memories (ROMs), random access memories (RAMs), and flash memories. Examples of computer programs include not only machine language codes created by a compiler, but also high-level language codes that are capable of being executed by a computer by using an interpreter or the like. The described hardware devices may be configured to act as one or more software modules to perform the operations of the above-described embodiments, or vice versa.

While embodiments have been shown and described with reference to the accompanying drawings, it will be apparent to those skilled in the art that various modifications and variations may be made from the foregoing descriptions. For example, adequate effects may be achieved even if the foregoing processes and methods are carried out in different order than described above, and/or the aforementioned elements, such as systems, structures, devices, or circuits, are combined or coupled in different forms and modes than as described above or be substituted or switched with other components or equivalents. Therefore, other implements, other embodiments, and equivalents to claims are within the scope of the following claims.

The invention claimed is:

1. A video conference image-based social anxiety treatment system for treating social anxiety using biofeedback and exposure therapy, the system comprising:

a bio-signal collection unit comprising a wearable terminal configured to collect a bio-signal of a subject during a speech task conducted through a video conference;

an anxiety level measurement unit comprising at least one processor configured to analyze the collected bio signal to measure, in real time, an anxiety level of the subject;

a video conference image provision unit comprising a display and a program executable by a processor, the program configured to provide video conference images to the subject via a user interface, the video conference images including a first face image of a real-time participant received via a participant terminal; and a second face image of a virtual participant retrieved from a database and having a pre-defined facial expression associated with an anxiety-inducing level; and an exposure therapy level adjustment unit comprising one or more processors configured to:

(i) measure an anxiety-inducing level of a facial expression of each participant from a plurality of real-time participant images exposed to the subject during the video conference;

(ii) select at least one first image from among the plurality of real-time participant images and a plurality of first virtual participant images currently exposed to the subject based on the measured anxiety-inducing levels of the respective images;

(iii) select at least one second image from among a plurality of second virtual participant images, which are not exposed to the subject, based on the anxiety level of the subject;

(iv) switch the first image, which is being exposed to the subject, with the second image and expose the second image to the subject through the video conference; and (v) transmit a guide phrase to a participant terminal to prompt a change in a facial expression of the real-time participant image, depending on the subject's anxiety level, (vi) wherein the video conference image provision unit is further configured to randomly and sequentially provide the plurality of real-time participant images and the plurality of first virtual participant images so as to simulate real-time access to the video conference at a participation time of the subject, and (vii) wherein the image switching unit is configured to randomly and sequentially switch a plurality of first images to a plurality of second images so as to simulate real-time access to the video conference when the plurality of first images are switched to the plurality of second images.

2. The system of claim 1, wherein the second face image includes a plurality of virtual participant images having different facial expressions and anxiety-inducing levels, wherein the plurality of virtual participant images includes a plurality of videos that are previously obtained from a plurality of virtual participants having an anxious facial expression, an indifferent facial expression, and a bright facial expression, and wherein the exposure therapy level adjustment unit is configured to adjust exposure ratios of the plurality of virtual participant images depending on the anxiety level of the subject.

3. The system of claim 2, wherein the first face image includes a plurality of real-time participant images of a plurality of participants actually participating in the video conference by using the participant terminal.

4. The system of claim 1, wherein the exposure therapy level adjustment unit is further configured to:

calculate a first anxiety-inducing level by summing anxiety-inducing levels from respectively measuring the plurality of real-time participant images;

calculate a second anxiety-inducing level by summing anxiety-inducing levels from respectively measuring the plurality of first virtual participant images; and select the plurality of first virtual participant images from among the plurality of virtual participant images such that a change amount of the second anxiety-inducing level offsets a change amount of the first anxiety-inducing level.

5. The system of claim 1, wherein the wearable terminal is worn on the subject and configured to collect the bio-signal of the subject, and wherein the anxiety level measurement unit comprising at least one processor is configured to measure the anxiety level of the subject from the bio-signal of the subject collected by the wearable terminal while the subject performs the speech task.

6. The system of claim 1, wherein the anxiety level measurement unit comprising at least one processor is configured to:

obtain a user image by photographing the subject by a camera while the subject performs the speech task; and measure the anxiety level of the subject by analyzing a facial expression of the subject and an action of the subject in the user image.

7. The system of claim 1, wherein, when the subject selects one category from among various categories of topics of the speech task, a sub-topic of the selected category is randomly selected and then is presented in a form of a pop-up.

8. A non-transitory recording medium having recorded thereon a computer program executable by a processor to perform a video conference image-based social anxiety treatment method using biofeedback and exposure therapy, the social anxiety treatment method comprising:

measuring, by a biofeedback sensor and the processor, an anxiety level of a subject during performance of a speech task through a video conference;

providing, by the processor, video conference images including a real-time participant image received from a participant terminal and a pre-recorded virtual participant image stored in a database, to a user interface for exposure therapy; and adjusting, by the processor, an exposure therapy level based on the measured anxiety level of the subject, the adjusting comprising:

(i) measuring respective anxiety-inducing levels of the real-time participant images and the virtual participant images currently displayed to the subject;

(ii) selecting at least one first image from among the displayed real-time and virtual participant images based on the respective anxiety-inducing levels;

(iii) selecting at least one second image, not currently displayed to the subject based on the measured anxiety level of the subject;

(iv) switching the displayed first image with the selected second image to adjust the exposure therapy level for the subject; and (v) transmitting a guide phrase to the participant terminal to prompt a change in a facial expression of the real-time participant image, (vi) wherein the providing and switching of images are performed randomly and sequentially to simulate spontaneous participant entry and turnover in the video conference based on changes in the subject's anxiety level.

9. The non-transitory recording medium of claim 8, wherein the virtual participant images comprise a plurality of pre-recorded videos having facial expressions including an anxious expression, an indifferent expression, and a bright expression, and wherein the processor adjusts an exposure ratio of each virtual participant image based on the anxiety level of the subject.

10. The non-transitory recording medium of claim 8, wherein the real-time participant image comprises video data streamed from a plurality of participant terminals.

11. The non-transitory recording medium of claim 8, wherein the processor calculates:

a first anxiety-inducing level by summing the anxiety-inducing levels of the currently displayed real-time participant images and determines a first change amount, a second anxiety-inducing level by summing the anxiety-inducing levels of the currently displayed virtual participant images and determines a second change amount, and selects the virtual participant images such that the second change amount offsets the first change amount to maintain a target exposure level for the subject.

* * * * *